United States Patent
Coughln

(10) Patent No.: US 7,491,220 B2
(45) Date of Patent: Feb. 17, 2009

(54) PLATE FOR FIXING THE BONES OF A JOINT, IN PARTICULAR A METATARSO-PHALANGEAL JOINT

(75) Inventor: Michael John Coughln, Boise, ID (US)

(73) Assignee: Newdeal S.A., Vienne (FR)

( * ) Notice: Subject to any disclaimer, the term of this patent is extended or adjusted under 35 U.S.C. 154(b) by 266 days.

(21) Appl. No.: 10/255,204

(22) Filed: Sep. 26, 2002

(65) Prior Publication Data
US 2003/0060827 A1   Mar. 27, 2003

(30) Foreign Application Priority Data
Sep. 26, 2001   (FR)   ................... 01 12417

(51) Int. Cl.
*A61B 17/70*   (2006.01)
(52) U.S. Cl. ..................................... 606/280
(58) Field of Classification Search ............. 606/69–71; 623/21.11, 21.15, 21.16, 21.17, 21.19; 248/200, 248/300, 301
See application file for complete search history.

(56) References Cited

U.S. PATENT DOCUMENTS

| | | | |
|---|---|---|---|
| 4,502,161 A * | 3/1985 | Wall .......................... | 623/14.12 |
| 4,800,874 A | 1/1989 | David et al. | |
| 4,923,471 A * | 5/1990 | Morgan ........................ | 606/60 |
| 4,966,599 A * | 10/1990 | Pollock ........................ | 606/69 |
| 5,021,056 A * | 6/1991 | Hofmann et al. ............... | 606/86 |
| 5,545,164 A * | 8/1996 | Howland ....................... | 606/61 |
| 5,676,667 A * | 10/1997 | Hausman ...................... | 606/69 |
| 5,718,704 A * | 2/1998 | Medoff ......................... | 606/69 |
| 5,718,705 A * | 2/1998 | Sammarco .................... | 606/69 |
| 5,853,413 A | 12/1998 | Carter et al. | |
| 6,206,883 B1 * | 3/2001 | Tunc ........................... | 606/77 |
| 6,221,073 B1 | 4/2001 | Weiss et al. | |
| 6,423,068 B1 * | 7/2002 | Reisberg et al. ............... | 606/69 |
| 6,730,091 B1 * | 5/2004 | Pfefferle et al. ................ | 606/70 |

FOREIGN PATENT DOCUMENTS

EP   1 132 052 A2   9/2001

* cited by examiner

*Primary Examiner*—Eduardo C Robert
*Assistant Examiner*—Mary Hoffman
(74) *Attorney, Agent, or Firm*—Thomas, Kayden Horstemeyer & Risley, LLP

(57) ABSTRACT

The invention relates to a plate for fixing the bones of a joint, in particular of a metatarso-phalanageal joint, for the purpose of performing arthrodesis, wherein:
  the plate comprises two sections, respectively a proximal section and a distal section, each section having a respective longitudinal axis of symmetry $S_1$, $S_2$ such that the projection onto a horizontal plane of tie axis of symmetry $S_2$ of the distal section presents an angle of inclination relative to the projection of the axis of symmetry $S_1$ of the proximal portion, the projections intersecting at a point A; and
  the projection onto a vertical plane of the axis of symmetry $S_2$ presents an angle of inclination relative to the projection of the axis of symmetry $S_1$, their intersection taking place at a point $A_2$ which is distinct from the point $A_1$.

19 Claims, 1 Drawing Sheet

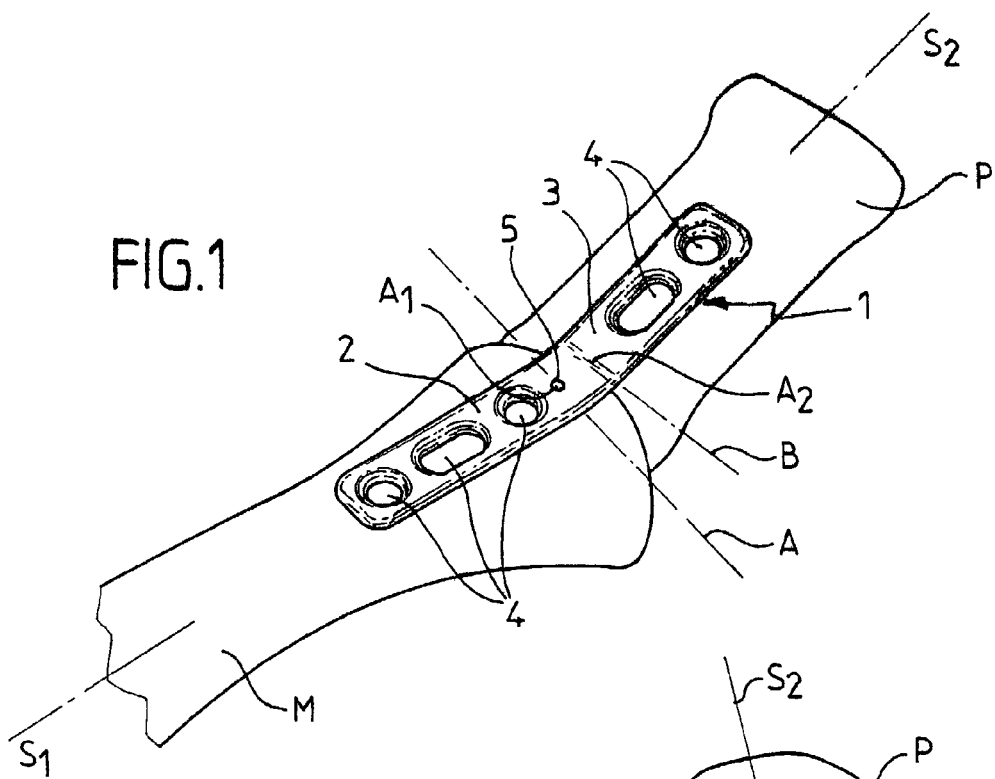
FIG.1
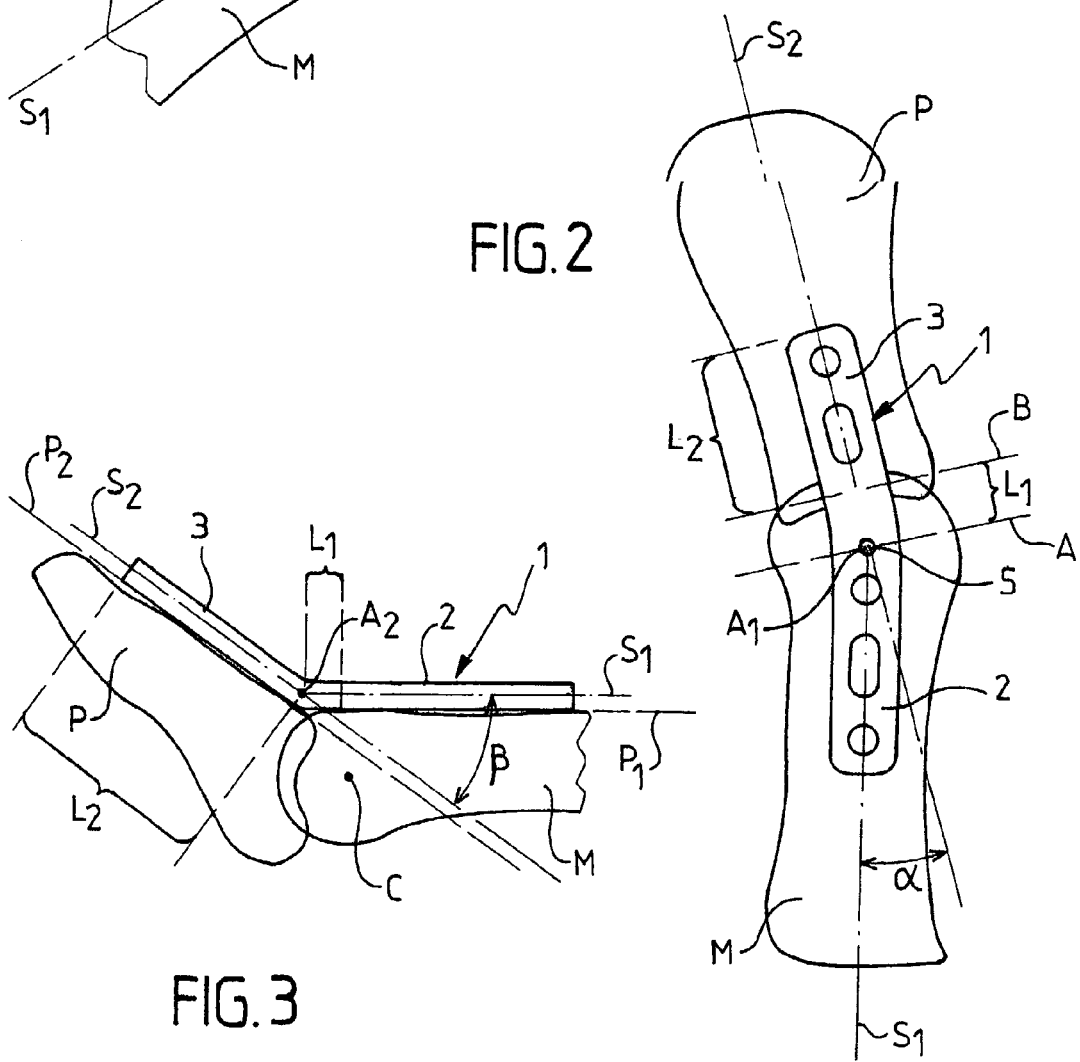
FIG.2
FIG.3

PLATE FOR FIXING THE BONES OF A JOINT, IN PARTICULAR A METATARSO-PHALANGEAL JOINT

FIELD OF THE INVENTION

The present invention relates to the general technical field of surgical devices for fixing together and aligning the two bony parts of a joint relative to each other, and in particular a joint including the phalanges of a toe or a finger in order to perform arthrodesis.

The present invention relates to a plate for fixing together the bones of a joint, in particular a metatarso-phalangeal joint, in order to perform arthrodesis.

In a preferred but non exclusive application of the invention, the fixing plate is more particularly, but not exclusively, intended and designed for setting an angular position and then performing arthrodesis on a metatarso-phalangeal joint. However, it should be understood that in the meaning of the invention applications to other joints can be envisaged, whenever the purpose is to bond the two bony parts of a joint together in a fixed relative position.

BACKGROUND OF THE INVENTION

In the event of arthrosis in joints between bones, and in particular in a metatarso-phalangeal joint, it is often necessary to perform arthrodesis in order to fuse the two bones together. As a general rule, arthrodesis constitutes an operation that is difficult in that it sets a joint in a position that is defined and it does so in a manner that is not reversible. Thus, it is very important for arthrodesis of a metatarso-phalangeal joint to be performed correctly insofar as the joint is involved as an essential actor in the walking cycle of a human being. It will thus be understood that it is essential for the two bones to be positioned relative to each other prior to fusion with an orientation that is implemented as accurately as possible in order to avoid any subsequent difficulty.

It is therefore essential for the axes of the bones to be fixed relative to each other so as to comply as well as possible with the flexing and the axes of the patient, and this must be done as a function of the patient's sex, gait, and morphology.

Until now, metatarso-phalangeal arthrodesis has been performed using fixing plates of a variety of shapes and provided with slots for receiving fixing screws in order to secure the plate to each of the two bones to be fused together.

Thus, by way of example, fixing plates are known that present a curved "quarter-tube" cross-section which the surgeon places across the joint between the bones to be fused together. That known plate is bent by the surgeon so as to take up an angle in the dorsi-flexion plane having a value that has been determined by the surgeon and that is specific to the patient. Once a joint has been blocked, plates of that type thus make it possible to confer a particular orientation in elevation on one of the two bones on which arthrodesis is performed. This constitutes an advantage to the patient since the joint is blocked under conditions close to normal conditions of use for that joint, thereby reducing difficulty for the patient while walking and reducing possible future complications. Nevertheless, fixing plates of that type turn out to suffer from a variety of drawbacks, and in particular they are quite difficult for the surgeon to bend. In addition, it turns out that bending is rarely performed with sufficient accuracy and that bending gives rise to deformed zones of the plate presenting edges that can be quite sharp and likely to generate irritation or inflammation on coming into contact with adjacent tissue such as tendons, muscles, ligaments, skin, etc. Finally, plates of that type are unsuitable for bending through a varus-valgus angle, which means that they are not capable of implementing arthrodeses that are sufficiently close to conditions of optimum geometrical orientation between the two bones to be fused together for the purpose of reducing to the greatest possible extent any risk of subsequent difficulties and complications for the patient.

Fixing plates that are completely plane are also known, and although they greatly reduce the risk of complications for the patient following the operation of installing them, insofar as no bending is performed, they nevertheless do not make it possible to perform an arthrodesis in which the bones present specific dorsi flexion and varus-valgus angles.

As a general rule, it also turns out that fixing plates for bending by the surgeon require a special bending tool to be used that is specific to each type of plate, thereby constituting a further constraint. Finally, it turns out that a fixing plate that has been bent suffers from weakening of its metal in the bend zone, and that can constitute a drawback in terms of strength. Furthermore, the need to provide openings through the plate for passing fixing screws complicates the operation of bending the plate, specifically because of the presence of said openings.

OBJECTS AND SUMMARY OF THE INVENTION

Consequently, the object of the invention is to remedy the various drawbacks set out above and to propose a novel plate for fixing the bones of a joint, in particular a metatarso-phalangeal joint, for the purpose of performing arthrodesis between two bone fragments under good conditions while ensuring that the relative orientation of the two bones to be fused together is determined with excellent accuracy.

Another object of the invention is to propose a novel plate for fixing the bones of a joint that makes it easier to put the plate into place and to seek a precise geometrical orientation.

Another object of the invention is to propose a novel plate for fixing the bones of a joint with improved placing of the plate.

Another object of the invention is to propose a novel plate for fixing the bones of a joint that is particularly well adapted to the anatomy of the bones to be fused together.

Another object of the invention is to propose a novel plate for fixing the bones of a joint that is suitable for being adapted to various possible anatomical configurations.

The objects given to the invention are achieved by means of a plate for fixing the bones of a joint, in particular a metatarso-phalangeal joint, for the purpose of performing arthrodesis, wherein:

the plate comprises two sections, respectively a proximal section and a distal section, each section presenting a respective longitudinal axis of symmetry $S_1$, $S_2$, said plate being designed to be placed across the joint, the axes $S_1$ and $S_2$ being parallel and aligned with the longitudinal axes of the two bone fragments to be fused together such that the projection onto a horizontal plane of the axis of symmetry $S_2$ of the distal section is inclined at an angle $\alpha$ relative to the projection of the axis of symmetry $S_1$ of the proximal portion, the projections intersecting at a point $A_1$; and the projection onto a vertical plane of the axis of symmetry $S_2$ presents an angle of inclination $\beta$ relative to the projection of the axis of symmetry $S_1$, the projections intersecting at a point $A_2$ which is distinct from the point $A_1$, the distal section extending over a first length fraction $L_1$ away from the proximal section while remaining in the same plane $P_1$ as the proximal section.

BRIEF DESCRIPTION OF THE DRAWING

Other advantages and objects of the invention appear in greater detail on reading the following description made with reference to the accompanying drawing that is provided purely by way of non-limiting explanation and in which:

FIG. 1 is a diagrammatic perspective view showing a plate for fixing the bones of a joint in order to perform arthrodesis, the plate being shown in position on a metatarso-phalangeal joint;

FIG. 2 is a plan view corresponding to a horizontal plane showing a plate of the invention for fixing together the bones of a joint, the plate turning to the left; and FIG. 3 is a fragmentary side view corresponding to a vertical plane showing a plate of the invention for fixing together the bones of a joint.

MORE DETAILED DESCRIPTION

FIGS. 1 to 3 show a fixing plate 1 in position and fixed to a metatarso-phalangeal joint for the purpose of performing arthrodesis between a metatarsal bone M and a phalangeal bone P.

Nevertheless, in the meaning of the invention, the fixing plate 1 of the invention could be used with appropriate anatomic shape and size for performing arthrodesis of some other joint, in particular for a joint in the hand when performing surgery of the hand.

The fixing plate 1 of the invention is in the form of an elongate body of plane cross section, for example, e.g. made of metal and of sufficient stiffness to provide a junction between the bones of the joint that are to be fused together and to provide firm support.

In accordance with the invention, the fixing plate 1 comprises two sections 2 and 3, respectively a proximal section and a distal section, each section presenting its own longitudinal axis of symmetry, respectively referenced $S_1$ and $S_2$.

Each section 2, 3 can thus be considered in general terms as a body having a thickness of a few millimeters and a length L that is longer than its width λ, so as to form a geometrical shape that is approximately that of a rectangular parallelepiped.

The proximal section 2 is for placing and fixing substantially on the metatarsal bone M, while the distal section 3 is for placing and fixing substantially on the phalangeal bone P in order to perform arthrodesis between these two bone fragments, the plate 1 thus being placed across the joint, with the axes of symmetry $S_1$ and $S_2$ being parallel and in alignment with the longitudinal axes of symmetry of the bones.

In conventional manner, fixing is performed by means of screws (not shown in the figures) which the surgeon screws into the bones through a series of slots 4 formed in the fixing plate 1, and in particular in each of its sections 2, 3 for the purpose of passing the fixing screws.

As shown in the figures, the proximal section 2 is advantageously longer than the distal section 3 while being of equal thickness and of width that is likewise equal. Because the proximal section 2 is longer, it advantageously has a larger number of orifices 4, for example it has three orifices while the distal section 3 has two orifices 4, and the orifices can be of any suitable shape, for example circular or oblong.

Alternatively the distal and proximal sections 3 and 2 are advantageously of identical length. In any event, the distal and proximal sections 3 and 2 are adjacent and form a single part.

This dimensional characteristic enables the fixing plate to be better adapted to the anatomy of the bones to be fused together and it improves the supporting and holding ability of said plate.

Advantageously, the two sections 2 and 3 are plane and rectilinear, it being understood that in a variant the cross sections of the proximal section 2 and of the distal section 3 could be curved to some extent, preferably equally, so as to provide a better fit to certain particular anatomical configurations.

According to an important feature of the invention, and as shown in particular in FIG. 2, the axes of symmetry $S_1$ and $S_2$ are not in alignment with each other, but on the contrary present a certain angle of inclination so that the two sections present respective inclinations in the horizontal plane. Thus, in accordance with the invention, the projection of the axis of symmetry $S_2$ of the distal section 3 onto a horizontal plane presents an angle of inclination α relative to the projection of the axis of symmetry $S_1$ of the proximal portion 2, these projections intersecting at a point $A_1$.

This feature makes it possible to impart an accurate and pre-established varus-valgus angle on the phalangeal bone relative to the metatarsal bone, the axes of symmetry $S_1$ and $S_2$ of the plate 1 being intended for mounting by a surgeon so as to be strictly parallel to the longitudinal axes of the two bone fragments M and P that are to be fused together.

In accordance with the invention, this angle of inclination α lies in the range 5° to 20° and is preferably about 10. It is specified that the angle of inclination α between the proximal and distal sections 2 and 3 is of a value that is fixed and specific to the fixing plate 1 of the invention, thus avoiding any need for the surgeon to bend the plate during the operation as is the case in the known prior art. The distal section 3 can be inclined either to the left or to the right relative to the proximal section 2.

According to another important characteristic of the invention, the fixing plate 1 is such that the projection onto a vertical plane (FIG. 3) of the axis of symmetry $S_2$ presents an angle of inclination β relative to the projection of the axis of symmetry $S_1$, these projections intersecting at a point $A_2$ which is distinct from the point $A_1$.

According to this important characteristic of the invention, and as shown in particular in FIGS. 1 and 3, the distal section 3 extends away from the proximal section 2 over a first length fraction $L_1$ while lying in the same plane $P_1$ as the proximal section 2, said first length fraction $L_1$ being extended by a second length fraction $L_2$ which extends in a plane $P_2$ forming an angle with said plane $P_1$, and specifically the angle β. The angle β enables the phalangeal bone P to be given a dorsi-flexion angle that is accurate and pre-established.

According to this characteristic, the sum of the lengths $L_1$ and $L_2$ corresponds to the total length of the distal section 3 starting from the line of inclination A (FIG. 1) marking the change in direction between the two sections 2 and 3. Thus, the proximal and distal sections 2 and 3 are connected together directly without a connection zone, and they are tangential to the single radius of curvature forming their connection.

According to this characteristic, the fixing plate of the invention has two distinct inclinations, one in the horizontal plane corresponding to the line A and to the angle α responsible for the varus-valgus angle, and the other corresponding to the line B and to the angle β responsible for the dorsi-flexion angle, the two inclination zones of the plate not coinciding, but on the contrary being offset from each other, with the change of inclination B being situated in a position that is distal relative to the line A.

Advantageously, the angle β lies in the range 5° to 20°, and is preferably about 10°. This angle β can be modified by the surgeon before or during surgery.

This disposition makes it possible to obtain a better match between the fixing plate 1 and the various bony parts to be fused together, since only the terminal fraction $L_2$ of the distal section 3 presents two angles of inclination, one in the horizontal plane and the other in the vertical plane, while the other fraction of the distal section presents only one angle of inclination, which angle is in the horizontal plane.

According to a particularly advantageous characteristic of the invention, the fixing plate 1 is provided with an intermediate fixing orifice 5. Advantageously, the intermediate fixing orifice 5 is situated at the intersection of the axes of symmetry $S_1$ and $S_2$, i.e. on the inclination line A, and it corresponds to the point $A_1$. This orifice enables the surgeon to fix the fixing plate 1 temporarily in register with the center C of the head of the metatarsal bone M by means of a pin prior to installing the final fixing screws through the slots 4.

The fixing plate of the invention is put into place as follows: after making an incision over the joint to be fused, the surgeon mills or cuts the faces of the joint so as to remove the arthrodesis present in the joint. Thereafter the surgeon puts the two bones to be fused together into position relative to each other and places the fixing plate 1 of the invention on the top faces of the bones M and P.

This positioning must be done while taking care to ensure that the fixing plate 1 is placed in such a manner that its axes of symmetry $S_1$ and $S_2$ are strictly parallel and aligned with the longitudinal axes of the two bone fragments M and P to be fused together. The surgeon must also take care to position the proximal section 2 in such a manner that the intermediate fixing orifice 5 is substantially in register with the center C of the head of the metatarsal bone M so as to achieve the best possible match between the plate and the bony parts. Fixing proper of the bones in the required geometrical configuration is then performed naturally because of the two natural angles of inclination of the fixing plate of the invention, which angles are fixed and pre-established.

The fixing plate of the invention thus makes it possible simply, quickly, and accurately to perform arthrodesis of the bones of a joint in a geometrical configuration that is accurate and pre established.

What is claimed is:

1. A plate for fixing the bones of a metatarso-phalangeal joint in order to perform arthrodesis, comprising:
    a proximal section and a distal section, each section presenting a respective longitudinal axis of symmetry $S_1$, $S_2$, said plate being designed to be placed across the metatarso-phalangeal joint, the axes $S_1$ and $S_2$ capable of being parallel and aligned with the longitudinal axes of the two bone fragments to be fused together such that a projection onto a horizontal plane of the axis of symmetry $S_2$ of the distal section is inclined at a pre-established non-zero angle α relative to a projection of the axis of symmetry $S_1$ of the proximal section, the projections intersecting at a point $A_1$; and
    a projection onto a vertical plane of the axis of symmetry $S_2$ presents a pre-established non-zero angle of inclination β relative to the projection of the axis of symmetry $S_1$, the projections intersecting at a point $A_2$ which is distinct from the point $A_1$, the distal section extending over a first length fraction $L_1$ away from the proximal section while remaining in a same plane $P_1$ as the proximal section and the distal section further extending over a second length fraction $L_2$ away from the proximal section that is in a different plane $P_2$ from the plane $P_1$; and said plate having sufficient stiffness to provide firm support to fuse the joint together.

2. A plate according to claim 1, wherein the pre-established angle of inclination α lies in the range 50° to 20°, and the pre-established angle β lies in the range 5° to 20°.

3. A plate according to claim 1, wherein the pre-established angle of inclination α is about 10° and the pre-established angle of inclination β is about 10°.

4. A plate according to claim 1, having a plurality of slots for passing a plurality of fixing screws.

5. A plate according to claim 1, having an intermediate fixing orifice for passing a fixing screw, the orifice being situated at the intersection of the axes of symmetry $S_1$ and $S_2$.

6. A plate according to claim 1, wherein the proximal section is longer than the distal section.

7. A plate according to claim 1, wherein the distal and the proximal sections are identical in length.

8. A plate according to claim 1, wherein the distal and the proximal sections are planar.

9. A plate according to claim 1, wherein the distal section is turned to the left or the right relative to the proximal section.

10. A plate for fixing bones, the plate comprising:
    a proximal section and a distal section, each section presenting a respective longitudinal axis of symmetry $S_1$, $S_2$, the axes $S_1$ and $S_2$ configured to be parallel and aligned with respective longitudinal axes of two bone fragments to be fused together such that a projection onto a horizontal plane of the axis of symmetry $S_2$ of the distal section is inclined at a fixed pre-established non-zero angle α relative to a projection of the axis of symmetry $S_1$ of the proximal section, the projections intersecting at a point $A_1$; and
    a projection onto a vertical plane of the axis of symmetry $S_2$ presenting a fixed pre-established non-zero angle of inclination β relative to the projection of the axis of symmetry $S_1$, the projections intersecting at a point $A_2$ which is distinct from the point $A_1$, the distal section extending over a first length fraction $L_1$ away from the proximal section while remaining in a same plane $P_1$ as the proximal section and the distal section further extended away from the proximal section by a second length fraction $L_2$ that is in a different plane $P_2$ from the plane $P_1$; and said plate having sufficient stiffness to provide firm support.

11. The plate of claim 10, wherein the proximal section and the distal sections are connected directly together.

12. The plate of claim 11, wherein the sum of the length fractions $L_1$ and $L_2$ is the entire length of the distal section.

13. The plate of claim 10, wherein the first length fraction $L_1$ and a portion of the length fraction $L_2$ have a substantially similar width.

14. A surgical device in the form of an elongate body comprising:
    a plate having a plurality of holes for receiving respective screws to fix the plate to at least one bone, wherein the plate further comprises:
        a first portion comprising an elongate body extending along a first axis through a first plane and comprising at least one of the plurality of holes; and
        a second portion comprising an elongate body comprising at least one of the plurality of holes, the second portion comprising a first length and second length, the first length extending along a second axis and through the first plane, the second axis of the first length having a fixed pre-established non-zero angle α with respect to the first axis of the first portion, the second length of the second portion extending along a third axis and through a second plane different from the first plane, the second plane of the second length having a fixed pre-established non-zero angle β with respect to the first plane, wherein the first portion is extended by the first length of the second portion, and the first length is extended by the second length of the second portion; and said plate having sufficient stiffness to provide firm support.

15. The plate of claim 14, wherein the first portion and the second portions are adjacent.

16. The plate of claim 14, wherein each of the first and second portions form a geometrical shape that is approximately a rectangular parallelepiped.

17. The plate of claim 14, wherein each of the first and second portions form a geometrical shape that is approximately a rectangular parallelepiped.

18. The plate of claim 17, wherein the cross-section of at least one of the first and second portions is curved.

19. The plate of claim 14, wherein the cross-section of at least one of the first and second portions is curved.

\* \* \* \* \*